United States Patent
Djurovic

(10) Patent No.: US 11,813,169 B1
(45) Date of Patent: Nov. 14, 2023

(54) ANATOMY PRESERVING SHOULDER JOINT REPLACEMENT DEVICE WITH NARROW SPHERICAL BEARING ARTICULATOR-INTERPOLATION SEGMENT

(71) Applicant: Zarija Djurovic, Chicago, IL (US)

(72) Inventor: Zarija Djurovic, Chicago, IL (US)

(*) Notice: Subject to any disclaimer, the term of this patent is extended or adjusted under 35 U.S.C. 154(b) by 445 days.

(21) Appl. No.: 17/241,222

(22) Filed: Apr. 27, 2021

(51) Int. Cl.
*A61F 2/40* (2006.01)
*A61F 2/30* (2006.01)

(52) U.S. Cl.
CPC ........ *A61F 2/4003* (2013.01); *A61F 2/30749* (2013.01); *A61F 2/4081* (2013.01); *A61F 2002/3085* (2013.01); *A61F 2002/30649* (2013.01); *A61F 2002/30909* (2013.01); *A61F 2002/4007* (2013.01); *A61F 2310/00023* (2013.01)

(58) Field of Classification Search
CPC ........... A61F 2/4003; A61F 2002/4007; A61F 2002/4011; A61F 2/4014; A61F 2002/4018; A61F 2/4081; A61F 2002/3241; A61F 2/34; A61F 2002/3414; A61F 2002/30624; A61F 2002/30634; A61F 2002/30635; A61F 2002/30649; A61F 2002/3065; A61F 2002/30652; A61F 2002/30632; A61F 2002/30471; A61F 2/30749; A61F 2002/30894; A61B 17/86; A61B 17/80
See application file for complete search history.

(56) References Cited

U.S. PATENT DOCUMENTS

| | | | | |
|---|---|---|---|---|
| 2,765,787 | A * | 10/1956 | Pellet | A61F 2/32 623/23.27 |
| 3,694,820 | A | 10/1972 | Scales et al. | |
| 3,815,157 | A | 6/1974 | Skorecki et al. | |
| 5,702,474 | A * | 12/1997 | McCandliss | A61F 2/32 623/13.12 |
| 5,951,605 | A * | 9/1999 | Dennis | A61F 2/32 623/13.11 |
| 6,328,764 | B1 * | 12/2001 | Mady | A61F 2/4081 623/22.16 |
| 6,488,716 | B1 * | 12/2002 | Huang | A61F 2/3601 623/23.12 |

(Continued)

OTHER PUBLICATIONS

Non-Final Office Action—dated Feb. 26, 2019 in related case U.S. Appl. No. 15/873,278, now abandoned.

(Continued)

*Primary Examiner* — Alvin J Stewart
(74) *Attorney, Agent, or Firm* — Clifford H. Kraft

(57) ABSTRACT

A human shoulder replacement that includes a housing with a narrow bearing articulator that can rotate to achieve the range of motion of a normal shoulder joint. The narrow bearing articulator contains a partially spherical bearing. The narrow bearing articulator fits into a housing that itself is recessed into a cavity cut into the Glenoid Fossa. The housing is typically a short cylindrically shaped receptacle that is screwed into the bone. The bearing has a shaft that passes through a drilled hole in the Humerus. The shaft is bolted at its distal end with a head that can be recessed into the Humerus. A penetrating screw is driven through a plate attached to the Humerus, through the Humerus itself, and through a hole in the shaft in the interior of the Humerus.

20 Claims, 2 Drawing Sheets

(56) References Cited

U.S. PATENT DOCUMENTS

| | | | | |
|---|---|---|---|---|
| 6,503,281 | B1* | 1/2003 | Mallory | A61B 17/8061 623/22.11 |
| 6,616,697 | B2* | 9/2003 | Sotereanos | A61F 2/3601 623/23.26 |
| 7,179,259 | B1* | 2/2007 | Gibbs | A61F 2/4603 606/98 |
| 7,909,882 | B2* | 3/2011 | Stinnette | A61F 2/4003 623/23.4 |
| 7,931,691 | B2* | 4/2011 | Li | A61F 2/3601 623/22.4 |
| 9,561,111 | B1* | 2/2017 | Goodman | A61F 2/40 |
| 2003/0171819 | A1* | 9/2003 | Sotereanos | A61B 17/744 623/908 |
| 2004/0260399 | A1* | 12/2004 | Chieng | A61F 2/3601 623/22.12 |
| 2005/0143745 | A1* | 6/2005 | Hodorek | A61B 17/1764 606/87 |
| 2006/0069443 | A1* | 3/2006 | Deffenbaugh | A61F 2/4081 623/19.11 |
| 2006/0074353 | A1* | 4/2006 | Deffenbaugh | A61B 5/036 600/587 |
| 2006/0161262 | A1* | 7/2006 | Chen | A61B 17/744 623/22.46 |
| 2006/0217720 | A1* | 9/2006 | Chieng | A61F 2/32 606/65 |
| 2007/0100458 | A1* | 5/2007 | Dalla Pria | A61F 2/4081 623/19.13 |
| 2007/0179624 | A1* | 8/2007 | Stone | A61F 2/4081 623/22.36 |
| 2007/0255420 | A1* | 11/2007 | Johnson | A61F 2/3601 623/22.44 |
| 2008/0004711 | A1* | 1/2008 | Li | A61F 2/3601 623/23.22 |
| 2008/0177395 | A1* | 7/2008 | Stinnette | A61F 2/34 606/60 |
| 2008/0255620 | A1 | 10/2008 | Strauss | A61B 17/7059 606/297 |
| 2009/0105838 | A1* | 4/2009 | Russo | A61F 2/4059 623/19.14 |
| 2012/0253467 | A1 | 10/2012 | Frankle | A61F 2/40 623/19.11 |
| 2014/0277521 | A1* | 9/2014 | Chavarria | A61F 2/4003 623/19.13 |
| 2014/0379089 | A1* | 12/2014 | Bachmaier | A61F 2/4014 623/19.14 |
| 2015/0335440 | A1* | 11/2015 | Linares | A61F 2/4003 623/19.12 |
| 2016/0022334 | A1 | 1/2016 | Bonutti | A61B 17/7233 606/62 |
| 2016/0045320 | A1* | 2/2016 | Klinger | A61F 2/3603 623/23.14 |
| 2016/0235539 | A1* | 8/2016 | Overes | A61F 2/40 |
| 2016/0374815 | A1* | 12/2016 | Siccardi | A61F 2/4003 623/19.12 |
| 2018/0092760 | A1* | 4/2018 | Sperling | A61F 2/4014 |
| 2018/0161169 | A1 | 6/2018 | Cardon | A61F 2/4081 |
| 2020/0323575 | A1* | 10/2020 | Cortes Cubero | A61F 2/3607 |
| 2021/0361440 | A1* | 11/2021 | Wang | A61F 2/30771 |
| 2022/0087825 | A1* | 3/2022 | Forsell | A61F 2/32 |
| 2022/0160514 | A1* | 5/2022 | Stockmans | A61F 2/4241 |
| 2023/0145329 | A1* | 5/2023 | Paterson | A61F 2/30756 623/19.14 |
| 2023/0157832 | A1* | 5/2023 | Chudik | A61F 2/30767 623/19.14 |
| 2023/0225772 | A1* | 7/2023 | Reed | A61B 17/7225 606/86 R |

OTHER PUBLICATIONS

Final Office Action—dated Oct. 30, 2019 in related case U.S. Appl. No. 15/873,278, now abandoned.

\* cited by examiner

ANATOMY PRESERVING SHOULDER JOINT REPLACEMENT DEVICE WITH NARROW SPHERICAL BEARING ARTICULATOR-INTERPOLATION SEGMENT

BACKGROUND

Field of the Invention

The present invention relates generally to medical joint replacement devices and more particularly to a very robust and efficient shoulder joint replacement device.

Description of the Problem Solved

Joint replacement devices are known in the art. In particular hip replacement devices and knee replacement devices are in use. There have been attempts at shoulder joint replacement as well. However, the human shoulder is a very complex and difficult joint to replace.

Skorecki in U.S. Pat. No. 3,815,157 describes a very early attempt at shoulder joint replacement. Scales in U.S. Pat. No. 3,694,820 teaches an early shoulder ball and socket prosthetic device. The problems with these prior art systems is that they are hard and sometimes dangerous for the patient to install, and they have a tendency to come lose. Also, metal parts may cause problems when implanted in the human body.

The human shoulder joint, or Glenoid or Glenoid Fossa, is located adjacent to, and partially under, a flat bone called the Clavicle or collarbone. The long upper arm bone, the Humerus has a rounded ball-shaped upper end that fits into the natural socket in the Scapula or shoulder blade. The surfaces of the bones are covered by cartilage, called Articular cartilage. A thin tissue called Synovial membrane covers the remaining surfaces. The membrane makes a fluid called Synovial fluid that provides lubrication for the joint. Replacement of the joint is usually attempted when either the cartilage is damaged or the bone itself has degenerated. This leads to considerable joint pain in the patient.

Replacement usually consists of replacing the ends of a damaged Humerus or a damaged Genoid, or both with plastic or metal parts that are typically held in place with cement, or are press-fit. There are about 53,000 shoulder replacements in the U.S. every year. One major problem is that after passage of time, the cement or press-fit components can break loose. In this case, further surgery is necessary. Failure also occurs because of wear, infection and dislocation that can be caused by the wearing or by some sort of further injury to the shoulder. In addition, replacement surgery is a complicated technique requiring a skilled surgical team.

It would be advantageous to have a shoulder replacement device that was attached to solid good bone using a partially spherical cavity that is screwed into the bone behind the Glenoid or joint that has a toleranced narrow bearing articulator part that rotates in the cavity and cannot escape from it. The bearing articulator part can be connected to the end of the Humerus with a shaft

SUMMARY OF THE INVENTION

The present invention relates to a human shoulder replacement that is surgically installed into the space of a patient's Glenoid Fossa after the Humerus is removed. This space or cavity in the Glenoid Fossa may need to be enlarged by the surgeon. The device includes a hollow housing containing a narrow spherical bearing articulator-interpolation segment that is mounted in the housing. The bearing articulator includes a cylindrical race that is also a mount post with an articulating partial spherical bearing portion. The bearing articulator fits into the housing, that itself is sunk into either the natural cavity in the Glenoid Fossa after the Humerus is removed, or an enlarged cavity in the Glenoid Fossa (depending upon the condition of the patient's shoulder). The housing is a short cylindrically shaped receptacle that can be screwed to the bone.

The bearing articulator contains a threaded extended shaft that's proximal end is screwed into the center of the bearing articulator, and that's distal end passes through a hole drilled in the Humerus. The distal end of the shaft is bolted to the Humerus with a nut that can be recessed into the bone. The shaft can also rest on a surface plate that fits over the proximal end of the Humerus and is connected to it with fishhook-like spikes or screws. Finally, a penetrating screw can be driven through an exterior rear plate attached to the Humerus, through the Humerus itself, and through a hole in the extended shaft in the interior of the Humerus. This screw keeps the bolted shaft from rotating.

DESCRIPTION OF THE FIGURES

Attention is now directed to several drawings that illustrate features of the present invention.

FIG. 2A shows the shaft pointing straight out.

Figure 1:
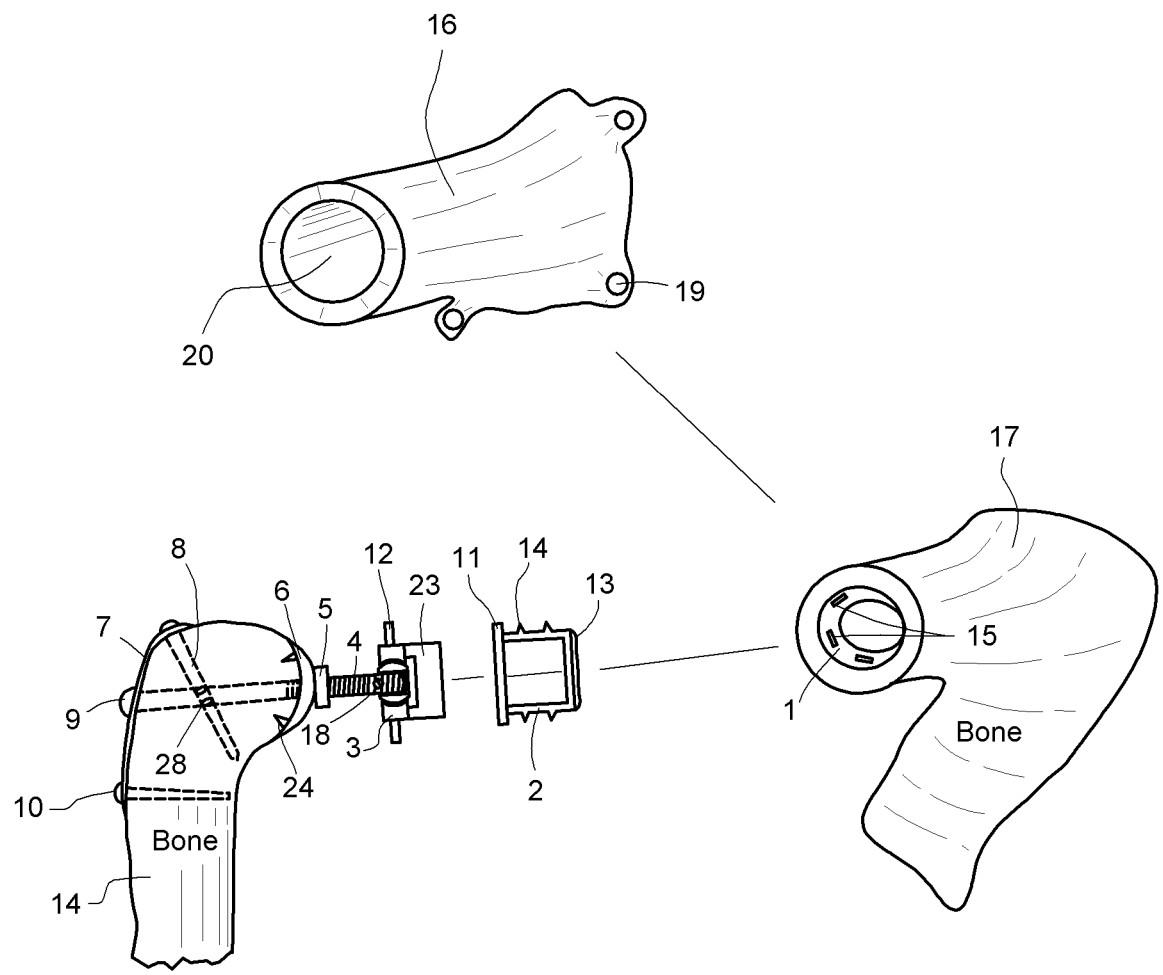
FIG. 1 shows an exploded view of an embodiment of the present invention.

Several figures and illustrations have been provided to aid in understanding the present invention. The scope of the present invention is not limited to what is shown in the figures.

DESCRIPTION OF THE PREFERRED EMBODIMENTS

The present invention relates to a human shoulder replacement device that is safe and relatively easy to install, and which is solidly attached to bone so that it cannot become dislodged.

Considering the anatomy of the human shoulder, the Humerus is the large arm bone that has a rounded ball-shaped head. In a healthy shoulder joint, the rounded head fits snuggly into a cavity in Glenoid Process or shoulder bone called the Glenoid Fossa. In the cavity, the bone surfaces are covered with Articular Cartilage that is associated with a surface membrane called the Synovial membrane. This membrane secrets Synovial fluid to lubricate the joint.

Several figures will be used to illustrate the invention. The following table is a key to reference numerals in the several figures:

1. Glenoid Fossa that is prepared to receive the articulator post that contains the bearing articulator;
2. Articulator post;
3. Narrow spherical bearing articulator—interpolation segment;
4. Threaded shaft inner portion;
5. Nut;
6. Humerus cap plate with spikes 7. Bone plate;
8. Shaft stabilizing screw;
9. Shaft outer portion;
10. Bone plate distal stabilizing screw;
11. Glenoid post plate to fit the bone of the Glenoid Fossa—medial surface and lateral to be rest for item 12. The position of 12 depends upon the size of the joint space;
12. Circular ring—interpolation regulator;
13. Stainless steel or other mesh for bone to grow on;
14. Two or more ribs and bone grooves of item 15 to interlock with a bone cement fixation;
15. Two or or more grooves in the bone;
16. Glenoidal clip housing squeezing the bearing articulator to the post, and the post to the bone with four or more screws;
17. Glenoid Process;
18. Set screw;
19. Clip housing lips with a threaded hole for torque control of the screw's fixation of process 16 to 17;
20. Frontal opening of 16 which is prepared to tightly fit on 3 on top of 12;
21. Bone cement space;
22. Screw hole;
23. Housing of bearing articulator;
24. Spike;
25. Screws connecting housing 2 to bone 1;
26. Screws connecting Glenoidal clip housing 16 to bone 1;
27. Semi-Spherical bearing part;
28. Hole in shaft 4.
29. Edge of Bearing Articulator It should be noted that the position of 12 depends on the joint space, which in turn will be different for different patients. The bigger the space, the more 12 should be placed medially so the interpolation segment will occupy the joint space. If the joint space is small, a small amount of bone on the Humerus capital side can be removed to increase the space for the proper position of the interpolation segment.

Turning to the figures, FIG. 1 shows an embodiment of the present invention. The Glenoid Process 17 or shoulder bone, and the Humerus 14 can be seen. The Articulator Glenoid post or housing 2 fits into a cavity 1, either the patient's natural cavity, or a cavity machined into the bone (if the patient's natural cavity is too small, it can be surgically enlarged). The housing 2 can be supplied in different sizes for different patients. Typically, a practitioner makes a 3-dimensional image model of the shoulder, and the size of the cavity 1 and housing 2 are predetermined based on dimensions of the patient's shoulder before surgery.

The cavity 1 in the Glenoid Fossa 17 is typically machined to have a flat mating surface and a circular groove 15 cut into the bone which can be continuous or a series of separated cuts as shown in FIG. 1. The articulator Glenoid post or housing 2 can have optional protrusions 14. A cement space 21 (shown in FIGS. 2A-2B) exists between the interior of the cavity 1 and the housing 2. The circular grove 15 aids the cement in holding the housing 2. Once installed in the cavity 1, the housing 2 is screwed down (shown in FIG. 2).

The bearing articulator 3 fits snugly into the housing 2. FIG. 1 shows the bearing articulator 3 with a bearing articulator housing 23. The housing 2 typically has a circular flat lip or ring 11 with a center hole sized to receive the bearing articulator 3. A circular ring 12 on the bearing articulator 3 encounters the lip 11 when the bearing articulator 3 is inserted into the housing 2 (also shown in FIG. 2). The bottom of the housing 2 can have a mesh surface 13 that promotes bone growth.

The lip 29 of bearing articulator stationary portion is trimmed so that when the bearing articulator 3 is inserted, the patient will have a full range of motion. The bearing articulator 3 can be pressed into the housing 2 or spot welded with a cold laser or other technique.

The bearing articulator 3 has a removable extended, partially or fully threaded shaft 4 that includes a lock-down nut 5 and a set screw 18. The proximal end of the shaft 4 is threaded into the center of the bearing articulator 3. The set screw 18 holds the shaft 4 in the bearing articulator 3. A front plate 6 is spiked into the Humerus and held in place by the lock-down nut 5. Plate 6 can optionally be screwed to the bone. A rear plate 7 is screwed 10 to the distal surface of the Humerus. The shaft 4 is run through the front plate 6 and the rear plate 7. A head 9, optionally recessed, holds the distal end of the shaft 4 to the plate 7 and hence the humerus 14. The nut 5, which can be a locking type nut or have a lock washer or even safety wire, secures the shaft 4 to the Humerus 14 against a front plate 6 that itself is screwed or spiked 24 into the Humerus.

A penetrating screw 8 passes through the plate 7 and through a cylindrical hole 28 in the shaft 4. This keeps the shaft 4 from rotating. This screw 8 can be guided in using x-rays or other imaging techniques. The penetrating screw 8 firmly prevents the shaft 4 from rotating or moving longitudinally.

A Glenoidal clip housing 16 with a opening 20 fits over the assembly and holds it together. The clip housing 16 is screwed to the bone 17 through a set of screw holes 19. The clip housing 16 is installed onto the Glenoid Fossa after the housing 2 with the bearing articulator 3 is inserted into the cavity 1. The shaft 4 is rotated on its threads into the threaded center of the bearing articulator 3 after the clip housing 16 is screwed down. The shaft 4 is locked to the bearing articulator 3 with the set screw 18.

Figure 2A:
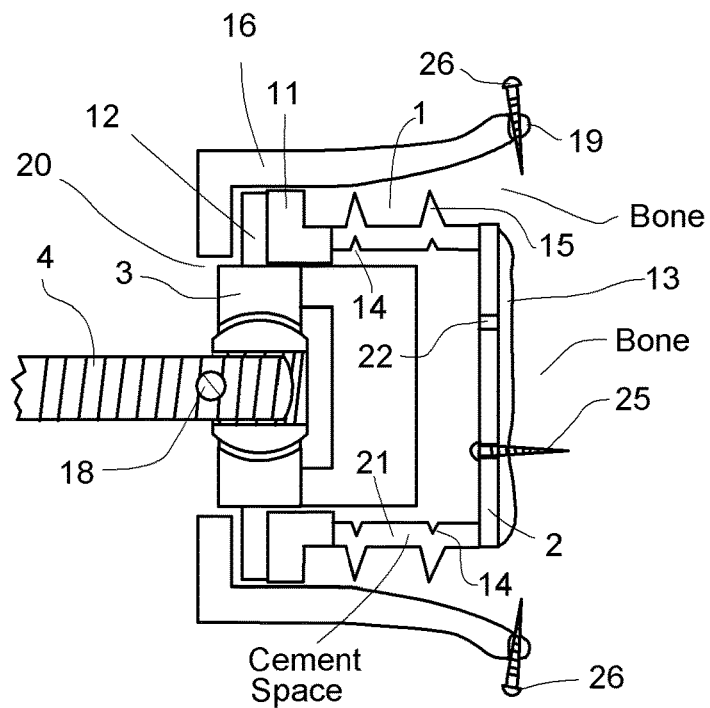
FIG. 2A shows the bearing articulator installed in the housing which is itself attached to the Glenoid Fossa.

Turning to FIG. 2A, a close-in assembled view of the apparatus can be seen. The housing 2 is inserted into the hole 20 in the bone. Protrusions 14 and the groove in the bone 15 aid in holding the housing 2 in the bone with cement. The housing 2 is screwed into the bone with screws 25 that pass through holes 22. The screws 25 can take and angle of between 0 degrees (straight in) to approximately 45 degrees. The bearing articulator 3 fits into the housing 2 with the tab or ring 12 encountering the neck or ring 11 of the housing. The bearing articulator 3 is in the housing 2. The Glenoidal clip housing 16 is screwed to the Glenoid Process with screws 26 that pass through holes 19 in the clip housing 16. The screws 26 can take an angle between 90 degrees (vertical) and 45 degrees. The shaft 4 is attached and held to bearing articulator 3 with the set screw 18 as previously described. The set screw 18 keeps the threaded shaft from rotating in the threaded bearing articulator 3.

Figure 2B:
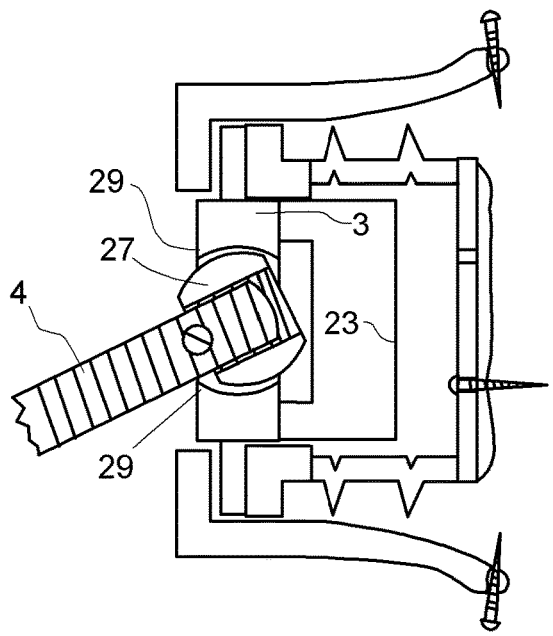
FIG. 2B is identical with FIG. 2A, except that the shaft is shown at an angle.

FIG. 2B shows the embodiment of FIG. 2A with the shaft 4 and the bearing articulator 3 at a downward sloping angle. The bearing articulator 3 is designed and machined to allow the full range of motion found in a natural shoulder joint. It can be seen in FIG. 2B that the bearing articulator has several parts, namely a fixed outer race and a partially spherical internal bearing member 27.

The present invention provides a robust shoulder replacement device that will not come loose due to cement. The bearing articulator is typically made of a metal or polymer and will not come apart. When metal is used, titanium is preferred; however, in some cases stainless steel may be used. Any rigid strong biologically compatible material is within the scope of the present invention.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A shoulder joint replacement device of a type that attaches a patient's humerus to the patients glenoid fossa providing a range of motion comprising:
   a housing constructed to be recessed into the patient's glenoid fossa;
   a narrow spherical bearing constructed to be placed in the housing, having a center part that rotates freely;
   a cover constructed to fit over a portion of the patients glenoid process, said cover allowing access to the narrow spherical bearing;
   an elongated shaft attachable to the narrow spherical bearing, the elongated shaft constructed to be passed through the patient's humerus;
   a penetrating screw also constructed to be passed through the patient's humerus and passing through the elongated shaft.

2. The shoulder joint replacement device of claim 1, further comprising a rear cover plate for the patient's humerus, the elongated shaft and the penetrating screw passing through the rear cover plate; heads on the elongated shaft and the penetrating screw engaging said cover plate.

3. The shoulder joint replacement device of claim 2, wherein the rear cover plate is constructed to be screwed or spiked to the patient's humerus.

4. The shoulder joint replacement device of claim 1 wherein the narrow spherical bearing is at least partially titanium.

5. The shoulder joint replacement device of claim 1 wherein the narrow spherical bearing is a polymer.

6. The shoulder joint replacement device of claim 1, wherein the elongated shaft is threaded on a proximal end.

7. The shoulder joint replacement device of claim 6 further comprising a nut threaded onto the elongated shaft, the nut constructed to hold the elongated shaft securely in the patient's humerus.

8. The shoulder joint replacement device of claim 1, wherein the elongated shaft is threaded into the narrow spherical bearing and secured with a set screw.

9. The shoulder joint replacement device of claim 1, wherein the housing has a bottom surface with an attached mesh.

10. A shoulder joint replacement device of a type that attaches a patient's humerus to the patients glenoid fossa providing a range of motion comprising:
    a housing constructed to be recessed into the patient's glenoid fossa;
    a narrow partially spherical bearing constructed to be placed in the housing, having a center part that rotates freely;
    a cover constructed to fit over a portion of the glenoid fossa, said cover allowing access to the narrow partially spherical bearing;
    an elongated shaft attachable to the partially spherical bearing, the elongated shaft constructed to be passed through the patient's humerus;
    a penetrating screw also constructed to be passed through the patient's humerus and pass through the elongated shaft;
    wherein, the elongated shaft is partially threaded with a nut constructed to anchor the elongated shaft to the patient's humerus.

11. The shoulder joint replacement device of claim 10, further comprising a rear cover plate for the patient's humerus, the elongated shaft and the penetrating screw passing through the cover plate; wherein heads on the elongated shaft and the penetrating screw engage said cover plate.

12. The shoulder joint replacement device of claim 11, wherein the cover plate is constructed to be screwed or spiked to the patient's humerus.

13. The shoulder joint replacement device of claim 10 wherein the narrow spherical bearing is at least partially titanium.

14. The shoulder joint replacement device of claim 10 wherein the narrow spherical bearing is a polymer.

15. The shoulder joint replacement device of claim 10, wherein the elongated shaft is threaded into the narrow spherical bearing and secured with a set screw.

16. The shoulder joint replacement device of claim 10, wherein the housing is cemented into a cavity in the patient's glenoid fossa.

17. The shoulder joint replacement device of claim 10, wherein the receiving member has a bottom surface with an attached mesh.

18. A method of providing a shoulder replacement comprising:
    providing a housing constructed to be recessed into the patient's glenoid fossa;
    providing a narrow spherical bearing constructed to be placed in the housing, having a center part that rotates freely;
    providing a cover constructed to fit over a portion of the patients glenoid process, said cover allowing access to the narrow spherical bearing;
    providing an elongated shaft attachable to the narrow spherical bearing, the elongated shaft constructed to be passed through the patient's humerus;
    providing a penetrating screw also constructed to be passed through the patient's humerus and passing through the elongated shaft.

19. The method of claim 18, further comprising providing a rear cover plate for the patient's humerus, the rear cover plate constructed to be screwed or spiked to the patient's humerus and wherein, the elongated shaft and the penetrating screw pass through the cover plate; and wherein heads on the elongated shaft and the penetrating screw engage said rear cover plate.

20. The method of claim 18, wherein edges of the narrow spherical bearing are trimmed or machined to allow a full range of motion of the patient's humerus.

* * * * *